United States Patent [19]

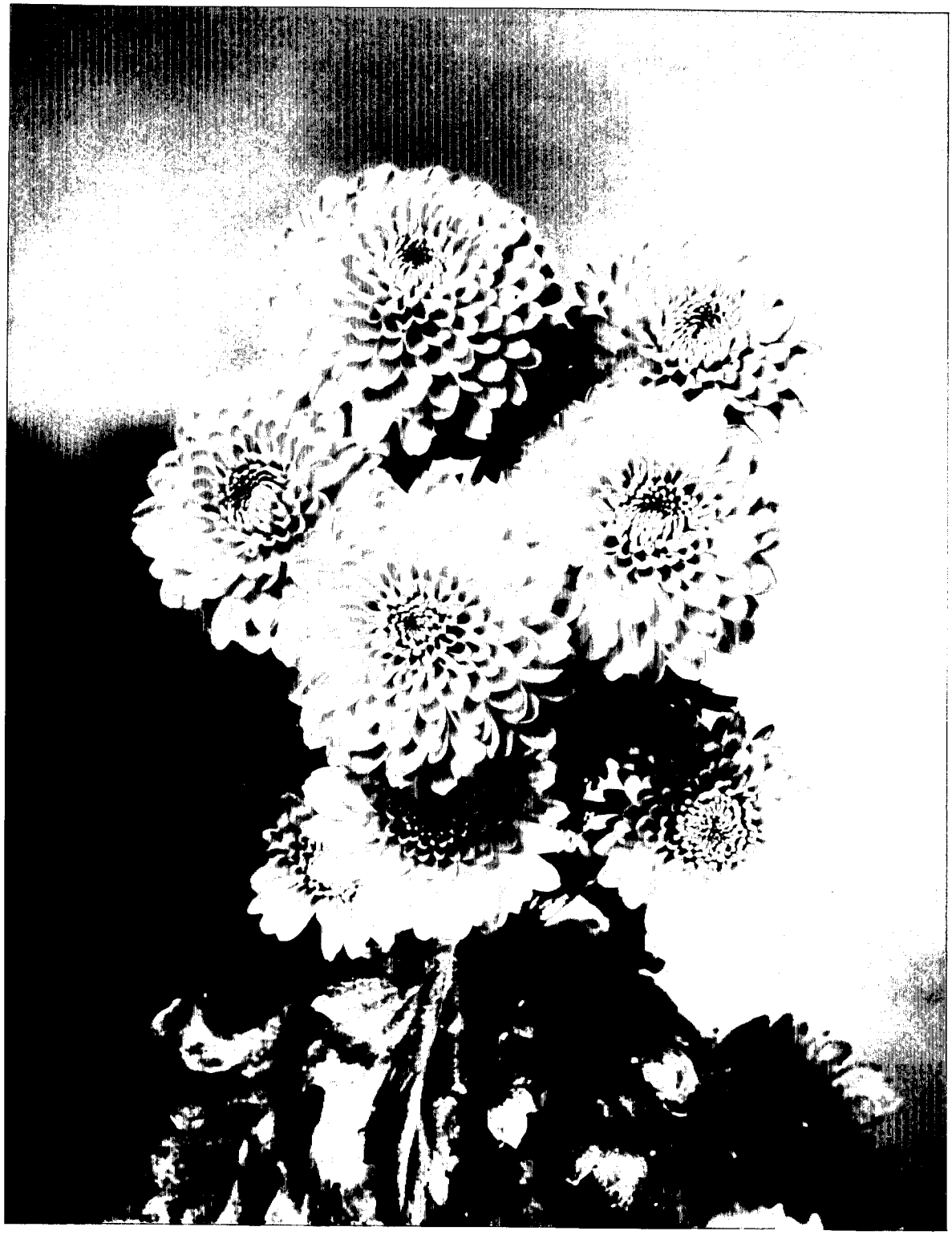

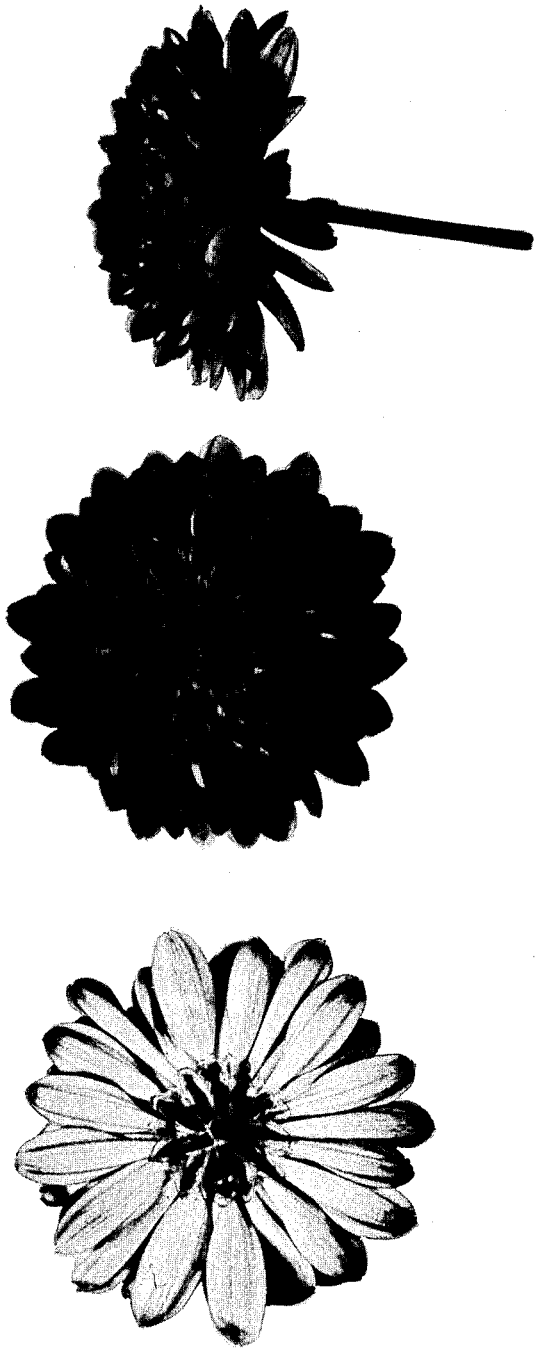

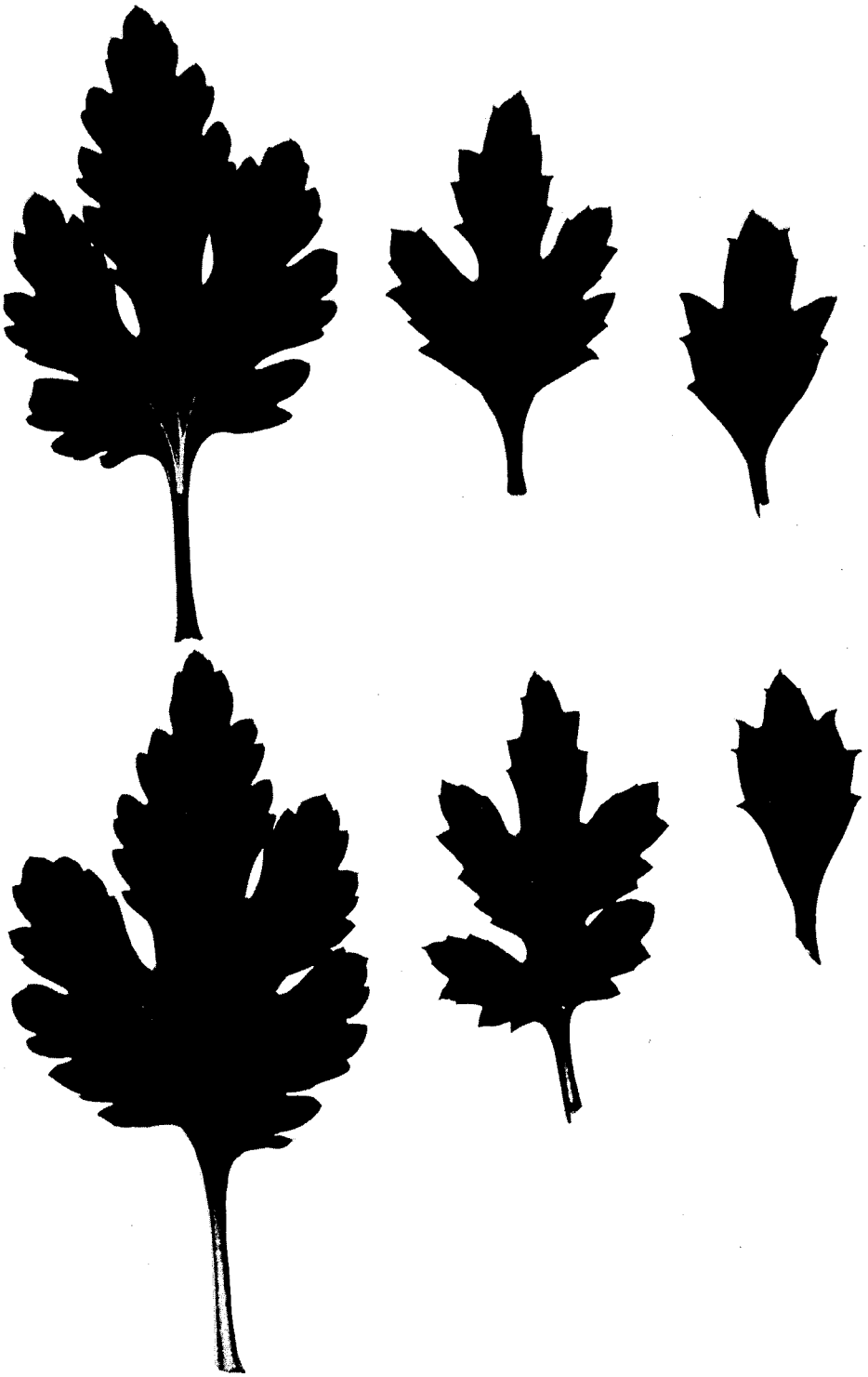

Duffett

[11] Patent Number: Plant 5,567

[45] Date of Patent: Oct. 1, 1985

[54] CHRYSANTHEMUM PLANT NAMED SUNUP

[75] Inventor: William E. Duffett, Salinas, Calif.

[73] Assignee: Yoder Brothers, Inc., Barberton, Ohio

[21] Appl. No.: 562,229

[22] Filed: Dec. 16, 1983

[51] Int. Cl.[4] ..... A01H 5/00

[52] U.S. Cl. ..... Plt./79

[58] Field of Search ..... Plt./79

*Primary Examiner*—Robert E. Bagwill

*Attorney, Agent, or Firm*—Schwartz, Jeffery, Schwaab, Mack, Blumenthal & Koch

[57] ABSTRACT

A new and distinct plant of *Chrysanthemum morifolium,* Ramat., named Sunup and particularly characterized as to uniqueness by the combined characteristics of round pompon capitulum form; formal decorative capitulum type; orange red ray floret color; diameter across face of capitulum ranging from 55 to 65 mm. at maturity; uniform eight week photoperiodic flowering response to short days; medium plant height when grown single stem; 12 to 18 cm. peduncles on open, normally terminal sprays; and 13° C. minimum temperature tolerance for initiation and development of flowering buds.

3 Drawing Figures

1

The present invention comprises a new and distinct cultivar of *Chrysanthemum morifolium,* Ramat., named Sunup.

Sunup is a product of a planned sport induction program which had the objective of creating new chrysanthemum cultivars that would expand the color range of high merit seedlings while retaining their other original traits.

Sunup was discovered and selected by William E. Duffett on Jan. 9, 1981 in a controlled environment in Salinas, Calif. as one flowering plant, a color variant within a flowering block established as rooted cuttings from stock plants which had been exposed as unrooted cuttings to an X-ray source of 900 rads. The irradiated clone was an unnamed seedling originated by the present inventor and identified as 79827002, an orange decorative. The parents of the immediate parent were similarly unnamed seedlings originated by the present inventor.

The first act of asexual reproduction of Sunup was accomplished when vegetative cuttings were taken from the initial selection in May 1981 in a controlled environment in Salinas, Calif. by a technician working under formulations established and supervised by William E. Duffett.

Horticultural examination of selected units initiated August 1981 has demonstrated that the combination of characteristics as herein disclosed for Sunup are firmly fixed and are retained through successive generations of asexual reproduction.

Sunup has not been observed under all possible environmental conditions. The phenotype may vary significantly with variations in environments such as temperature, light intensity and day length. The following observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Sunup, which in combination distinguish this chrysanthemum as a new and distinct cultivar:

(1) Round pompon capitulum form.

(2) Formal decorative capitulum type.

(3) Orange red ray floret color.

2

(4) Diameter across face of capitulum ranging from 55 to 65 mm. at maturity.

(5) Uniform eight week photoperiodic flowering response to short days.

(6) Medium peduncle length, ranging from 12 to 18 cm.

(7) Medium plant height, requiring 2 to 3 long day weeks prior to short days to attain a flowered plant height of 80 to 90 cm. for April through October flowerings with single stem procedure.

(8) Low temperature tolerance of 13° C. for initiation and development when grown in single stem cut spray programs with a continuous dark period of 13 hours.

The accompanying photographic drawings show typical inflorescence and leaf characteristics of Sunup, with the colors being as nearly true as possible with illustrations of this type. Sheet 1 is a color photograph of Sunup grown as a single stem cut spray. Sheet 2 is a black and white photograph of three views of the inflorescence of Sunup. Sheet 3 is a black and white photograph showing the leaves of Sunup at three stages of development (mature, intermediate and immature).

Of the many commercial cultivars known to the present inventor, the most similar in comparison to Sunup is Flame Belair, disclosed in U.S. Plant Pat. No. 3,353.

Reference is made to attached Chart A which compares certain characteristics of Sunup to those same characteristics of Flame Belair.

In comparison to Flame Belair, Sunup has slightly darker inflorescence color, more formal form, smaller diameter across face of capitulum, shorter peduncle length, shorter plant height, more rapid response to controlled short days and more uniform tolerance of 13° C. initiation and development temperatures.

In the following description, color references are made to The Royal Horticultural Society Colour Chart. The color values were determined between 9:00 and 9:30 A.M. on Jul. 28, 1983 under 150 foot-candle light intensity at Salinas, Calif.

Classification:

*Botanical.—Chrysanthemum morifolium,* Ramat., cv SUNUP.

*Commercial.*—Decorative Spray Cut Mum.

I. Inflorescence:

A. *Capitulum.*—Form: Round pompon. Type: Formal decorative. Diameter Across Face: 55 to 65 mm.

B. *Corolla of ray florets.*—Color (general tonality from a distance of three meters): Greyed orange/orange red. Color (abaxial): 171B–C oxidizing to 172D. Due to incurving, there is a shadowed color which approximates 34B–C. Color (adaxial): 13C flushed with 168D. Shape: Oblong with rounded tip.

C. *Corolla of disc florets.*—Color (mature): 14B. Color (immature): 154C.

D. *Reproductive organs.*—Androecium: Present dic florets only; scant pollen. Gynoecium: Present both ray and disc florets.

II. Plant:

A. *General appearance.*—Height: Medium; 65 to 75 cm., as a single stem flowering plant from a rooted cutting, with no long days for April through October flowerings and maintaining a minimum nightly 13 hour continuous dark period.

B. *Foliage.*—Color (abaxial): 147A. Color (adaxial): 147B. Shape: Deeply lobed and moderately serrated.

CHART A

COMPARISON OF SUNUP AND FLAME BELAIR

| | RAY FLORET | CAPITULUM FORM AND | SPRAY FORMA- | DIAMETER ACROSS FACE OF CAPIT- |
|---|---|---|---|---|

CHART A-continued

COMPARISON OF SUNUP AND FLAME BELAIR

| CULTIVAR | COLOR | TYPE | TION | ULUM |
|---|---|---|---|---|
| SUNUP | ORANGE RED | ROUND POMPON FORMAL DECORATIVE | 12 to 18 cm. PEDUNCLES | 55 to 65 mm. |
| FLAME BELAIR | ORANGE | FLAT DECORATIVE | 15 to 22 cm. PEDUNCLES | 75 to 90 mm. |

| CULTIVAR | PLANT HEIGHT | FLOWERING RESPONSE PERIOD | TOLERANCE OF 13° C. |
|---|---|---|---|
| SUNUP | 65 to 75 cm. | 8 WEEKS | GOOD UNIFORM |
| FLAME BELAIR | 80 to 90 cm. | 9 WEEKS | POOR UNEVEN |

COMPARISONS MADE OF PLANTS GROWN AS SINGLE STEM SPRAY CUT MUMS WITH NO LONG DAYS IN SALINAS, CALIFORNIA

I claim:

1. A new and distinct plant of *Chrysanthemum morifolium,* Ramat., named Sunup, as described and illustrated, and particularly characterized as to uniqueness by the combined characteristics of round pompon capitulum form; formal decorative capitulum type; organge red ray floret color; diameter across face of capitulum ranging from 55 to 65 mm. at maturity; uniform eight week flowering response; medium plant height when grown single stem; 12 to 18 cm. peduncles on open, normally terminal sprays; and 13° C. minimum temperatures tolerance for initiation and development of flowering buds.

* * * * *